United States Patent [19]
Stalker et al.

[11] Patent Number: 6,074,404
[45] Date of Patent: Jun. 13, 2000

[54] WOUND CLOSURE ASSEMBLY AND METHOD OF USE

[75] Inventors: Kent C. B. Stalker, San Diego; Bruce M. Wilson, Escondido, both of Calif.

[73] Assignee: Advanced Cardiovascular Systems, Inc., Santa Clara, Calif.

[21] Appl. No.: 09/338,368

[22] Filed: Jun. 23, 1999

Related U.S. Application Data

[63] Continuation of application No. 09/024,326, Feb. 17, 1998, Pat. No. 5,972,005.

[51] Int. Cl.[7] ................................................ A61B 17/04
[52] U.S. Cl. ........................................................ 606/144
[58] Field of Search .................................. 606/139, 144, 606/213, 145, 148, 222, 223, 224

[56] References Cited

U.S. PATENT DOCUMENTS

| | | |
|---|---|---|
| 5,181,919 | 1/1993 | Bergman et al. . |
| 5,222,508 | 6/1993 | Gimpelson . |
| 5,304,184 | 4/1994 | Hathaway et al. . |
| 5,320,632 | 6/1994 | Heidmueller ............................. 606/144 |
| 5,336,231 | 8/1994 | Adair ....................................... 606/148 |
| 5,364,408 | 11/1994 | Gordon ..................................... 606/144 |
| 5,368,601 | 11/1994 | Sauer et al. . |
| 5,374,275 | 12/1994 | Bradley et al. . |
| 5,391,182 | 2/1995 | Chin . |
| 5,403,329 | 4/1995 | Hinchcliffe ............................. 606/147 |
| 5,431,666 | 7/1995 | Sauer et al. . |
| 5,476,569 | 12/1995 | Hathaway et al. . |
| 5,496,332 | 3/1996 | Sierra et al. . |
| 5,527,321 | 6/1996 | Hinchliffe ............................... 606/144 |
| 5,665,096 | 9/1997 | Yoon . |
| 5,814,065 | 9/1998 | Diaz . |

FOREIGN PATENT DOCUMENTS

WO 94/13211  6/1994  WIPO .
WO 95/13021  5/1995  WIPO .

*Primary Examiner*—Michael Buiz
*Assistant Examiner*—Jackie Ho
*Attorney, Agent, or Firm*—Fulwider Patton Lee & Utecht, LLP

[57] ABSTRACT

A wound suturing assembly and method of use employing elastically precurved suture needles for piercing a patient's tissue to suture closed a wound. The needles are ejected out of the assembly and whereupon they assume a pre-curved shape and in the process curve back to pierce the tissue a second time prior to reentering the assembly. Each needle carries a length of suture through the wound so that the sutures can be tied and the wound tightly sealed.

13 Claims, 4 Drawing Sheets

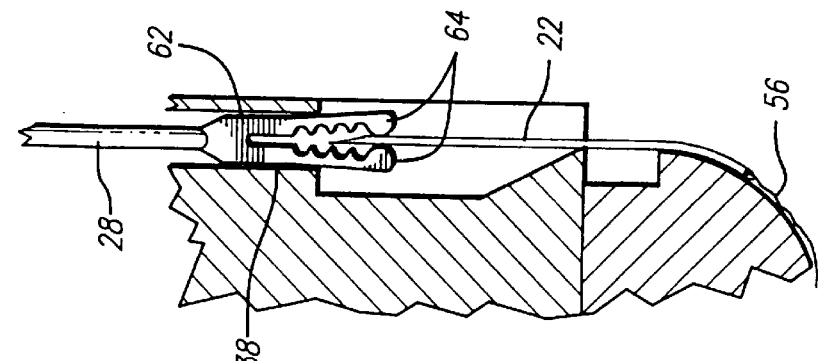
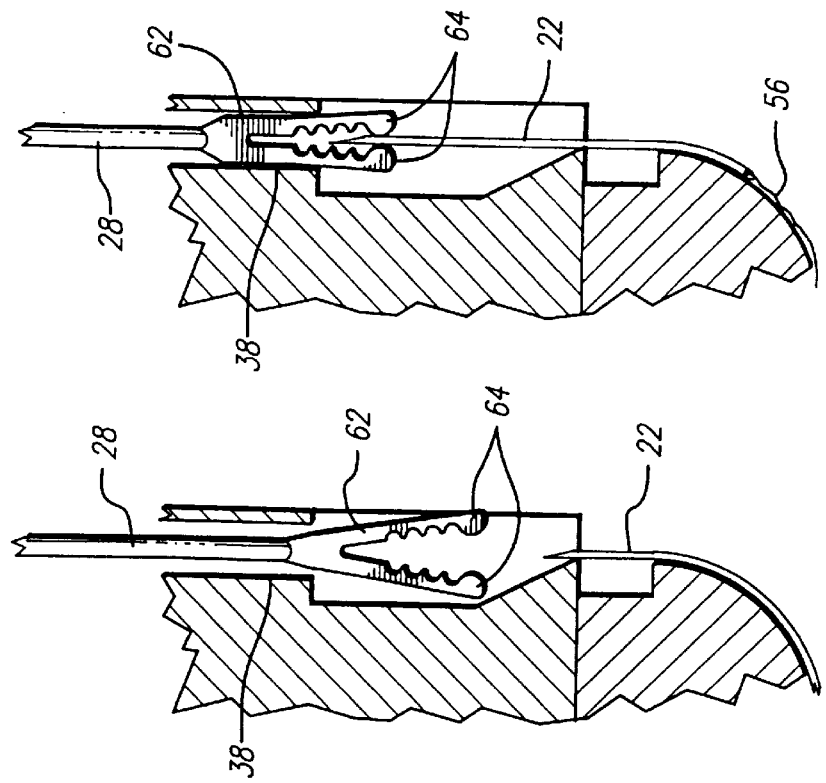
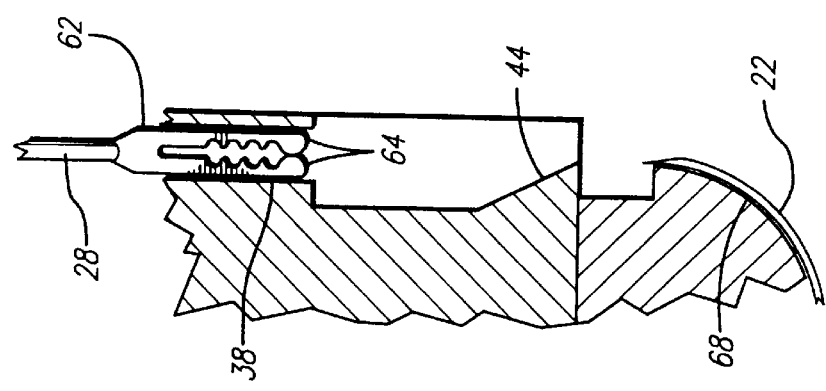
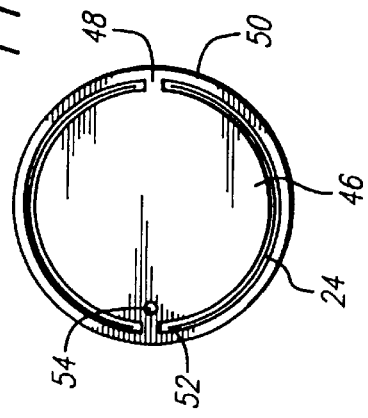
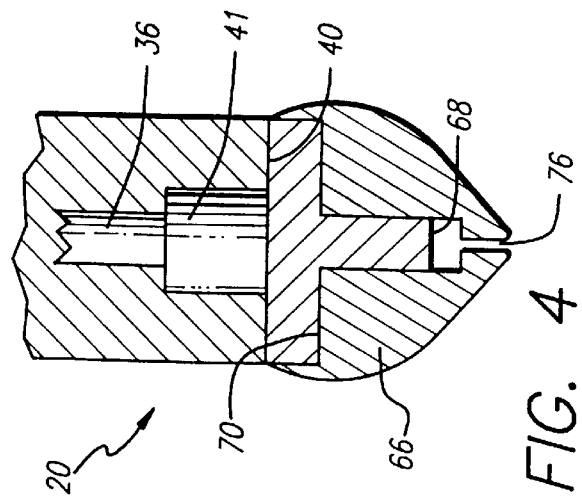

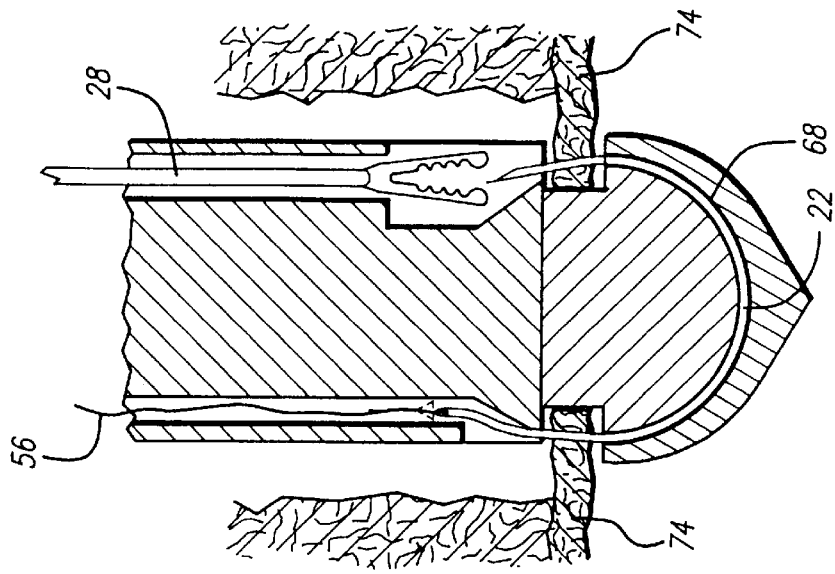
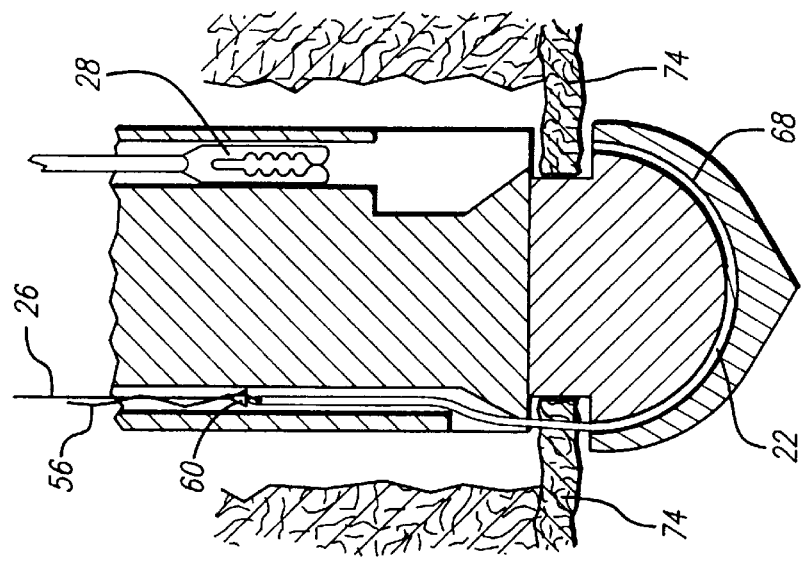
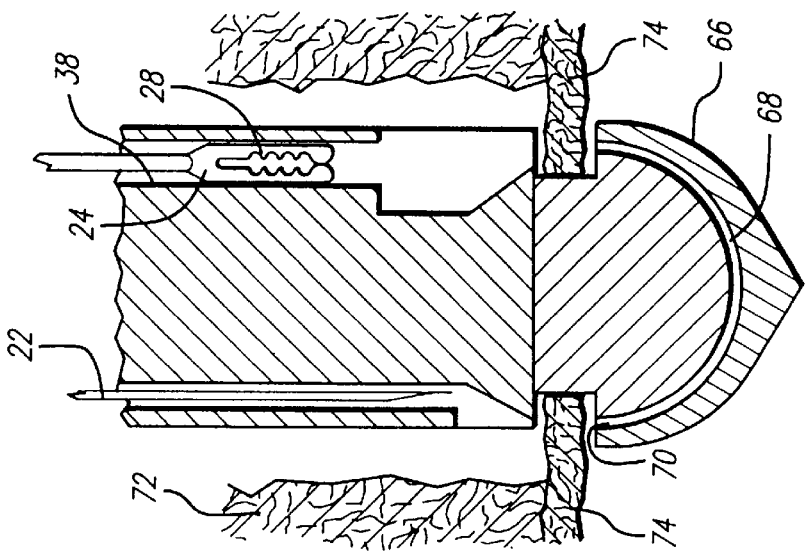

WOUND CLOSURE ASSEMBLY AND METHOD OF USE

This application is a continuation of U.S. Ser. No. 09/024,326 filed Feb. 17, 1998 U.S. Pat. No. 5,972,005.

BACKGROUND OF THE INVENTION

The present invention relates generally to an apparatus and method for the closure of wounds in body tissue, and more particularly to an apparatus and method for the suture of puncture sites in body lumens accessible through a tissue tract.

Transluminal medical procedures have seen a marked rise in popularity during the past decade due to the much reduced surgical damage to healthy tissue, recovery time, and ultimate cost to the patient associated with these procedures. Such procedures typically require an incision formed in a body lumen and the overlying tissue through which catheters, guide wires, laparoscopes, endoscopes, and similar medical devices can be inserted into the patient's vascular system. The incisions are created with instruments such as trocars, and may measure from 5 to upwards of 15 mm in diameter. After the intravascular procedure is complete, the incision must be closed and sealed as quickly as possible to prevent further bleeding.

Unfortunately, the size of the incision is usually large enough to permit profuse bleeding, but too small for the convenient application of conventional wound closure techniques such as suturing. Other methods have been proposed, including the use of collagen and other types of plugs placed outside the lumen and near the wound. Some plugs are designed to be placed directly within the lumen and secured against the inner wall of the lumen by an external suture attached to the plug. In yet other similar closure methods, a clotting agent such as a foam, gel, or powder is dispensed within the wound. These methods all tend to cause the at least partial deposition of a plug or clotting agent within the lumen, whether by design or unintentionally, and thus result in the partial occlusion of the flow of blood through the lumen near the site of the wound. This is an unfortunate side effect that can lead to complications such as thrombosis and is therefore undesirable.

Another common closure technique employs continuous pressure applied to the wound site to allow the patient's blood to clot sufficiently to seal the wound. This technique, however, is usually very time consuming for both patient and medical personnel, thus partially negating one of the main advantages of transluminal procedures. In addition, a hematoma may occur if the patient moves while the pressure is being applied and therefore additional rest and observation in the hospital is required, further driving up the cost and time associated with the procedure.

Sutures remain the preferred method of sealing wounds, but the small size of the typical wound formed during a transluminal procedure renders the application of sutures a delicate and difficult task. Traditionally the surgeon would introduce a suture needle through the tissue tract and into the body lumen, manipulate the needle with a grasping instrument into position, then urge it to penetrate and pass through the lumen wall near the wound site and pull the suture material therethrough. This procedure involves difficult manipulations and maneuvers in a small space and through a small opening, and is therefore time consuming and burdensome.

Due to the ever increasing number of transluminal procedures performed each year, a great deal of effort has been devoted to the development of quicker, safer methods for post-operative suturing of endoscopic wounds. Practically all viable methods involve the use of a specially developed device for placing sutures in the lumen and through the body tissue. Some devices employ needles to carry opposite ends of a suture through the tissue surrounding the wound, and then means for retrieving the ends of the suture from within the body lumen and out through the wound. Such means may include an expandable mesh (U.S. Pat. No. 5,496,332 to Sierra et al.), a flexible membrane capturing anchors attached to the ends of the suture (U.S. Pat. No. 5,391,182 to Chin), and an expandable bow assembly (U.S. Pat. Nos. 5,304,184 and 5,476,469 to Hathaway et al.). A drawback to the method employed by these devices is that the suture ends pass from within the lumen and out through the wound opening, and are thereby trapped between the tissue walls surrounding the wound when the suture is tensioned to close the opening. This suture configuration prevents the tissue walls from fully contacting each other and thus may require an extended period of time to heal. In addition, this configuration also requires that the suture knot tied by the surgeon must lie within the lumen, and therefore in most cases the surgeon cannot tie a sufficiently tight knot to prevent any further bleeding and to ensure minimal scarring of the tissue upon healing. Finally, most such devices require the surgeon to blindly capture the ends of the suture within the lumen while blood courses through the lumen with the patient's heart beat, making exact placement and capture of the suture ends difficult and imprecise.

Other suturing devices employ tubes carrying needles mounted on extendible platforms that advance out of the distal end of the tube once the distal end has been positioned within the lumen. The needles may be straight or curved, and carry sutures so that when the device is retracted from the lumen the needles pierce the side walls of the wound and thereby carry the sutures through the surrounding tissue. Devices of this type are disclosed in, e.g., U.S. Pat. No. 5,374,275 to Bradley et al., U.S. Pat. No. 5,364,408 to Gordon, U.S. Pat. No. 5,320,632 to Heidmueller, U.S. Pat. No. 5,403,329 to Hinchcliffe, U.S. Pat. No. 5,368,601 to Sauer et al., and international publications WO 94/13211 and WO 95/13021. A relatively similar device is disclosed in U.S. Pat. No. 5,431,666 to Sauer et al., wherein the device has a distal end with a suture equipped with ferules at either end placed therein. The distal end is positioned within the lumen and beneath the side walls of the wound, and sharp needles are driven through the side wall tissue to engage the ferules and pull the suture out. These devices are preferable because they create a cleaner, tighter seal of the wound, and are somewhat easier to operate because the suture ends do not have to be captured blindly within the lumen. Unfortunately, however, such devices are relatively complex and employ a significant number of moving parts. These devices are therefore relatively costly to manufacture and are also more prone to mechanical failure. In addition, such devices cannot be easily manufactured with very small diameters because of the complex mechanisms that must fit entirely within the device, especially when the needles are curved, and thus some of the devices may not be suited to suturing small diameter wounds.

The need continues to exist for a suturing method that will cleanly and tightly suture small as well as larger diameter wounds with an uncomplicated, dependable, inexpensive apparatus that is fail proof and simple to use. The present invention meets these needs.

SUMMARY OF THE INVENTION

Transluminal medical procedures are usually performed through an incision formed in a body lumen and the overlying tissue through which the catheters, guide wires, laparoscopes, endoscopes, and other medical devices required for the particular procedure can be inserted into the patient's vascular system. The incisions are created with instruments such as trocars and may measure from 5 to over 15 mm in diameter. After the intravascular procedure is complete, the incision must be closed and sealed as quickly as possible to prevent further bleeding. The size of the incision is usually too small for the convenient application of conventional wound closure techniques such as suturing, and unfortunately alternative methods that have been proposed suffer from other serious drawbacks.

The present invention provides for an apparatus and method for suturing small, as well as large, wounds in body tissue. In keeping with the invention, a guide body is provided that is adapted for retaining and handling needles for puncturing the patient's tissue.

The apparatus of the present invention provides a wound suturing device consisting primarily of elastically precurved needles maintained in a linear configuration within a guide body containing needle ejectors for ejecting the needles out of the body and needle receivers for receiving and retracting the needles back into the body. The needles are manufactured from resilient materials formed in elastically precurved configurations that begin to manifest as the needles are ejected from the apparatus and pierce the patient's tissue, and thus curve back towards the guide body and pierce the patient's tissue a second time to draw a length of suture therethrough and seal the wound shut.

The guide body is formed with pairs of parallel, laterally opposed bores for ejecting and receiving each needle, and has a semi-spherical guide tip at its distal end for guiding the needles and engaging the lumen wall tissue within grooves formed between the distal end and the guide tip. A needle ejector arm is positioned in the first of each pair of bores, and a forceps for receiving and grasping the needle is positioned in the corresponding second bore. Both needle ejector arms and receiving forceps are actuated by a single, common handle sliding within the guide body.

The method of use of the present invention entails threading suture through each needle and then positioning the needles within the respective ejection bores of the guide body. The guide body is next positioned with the distal end within the wound and the lumen tissue located directly underneath the bores, and the needles are then advanced by the ejector arms out of the ejection bores and through the lumen tissue, curved around the distal end, and pushed back through the lumen tissue and into the receiving bores where they are grasped by the receiving forceps and retracted back into the guide body. The guide body is then retracted out of the lumen, leaving behind lengths of suture passing through opposite sides of the lumen wall, which are then tied together to close and seal the wound.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 3 depicts a top view of the suturing apparatus shown in FIG. 1.

FIG. 4 depicts a partial cross-sectional side view of the suturing apparatus shown in FIG. 1 incorporating an alternative tip design.

FIGS. 5A–5C depict the operation of the needle receiver element of the suturing apparatus shown in FIG. 1.

FIGS. 6A–6C depict the operation of the needle element of the suturing apparatus shown in FIG. 1.

DETAILED DESCRIPTION OF THE PREFERRED EMBODIMENTS

Transluminal medical procedures require forming an incision in a lumen of the patient's body and the overlying tissue, through which catheters, guide wires, laparoscopes, endoscopes, and similar medical devices are inserted into the patient's vascular system to reach the target site or organ. The incision thus created may measure anywhere from 5 to over 15 mm in diameter. After the intravascular procedure is complete, the access incision must be closed and sealed tightly to prevent further bleeding and the occurrence of any post-operative complications. The size of the incision is typically not large enough to be amenable to the conventional application of sutures, and no alternative methods have been developed that accomplish this objective safely and effectively.

The present invention overcomes the limitations imposed by the small size of intraluminal procedure incisions and allows medical personnel to quickly, easily, and accurately suture such wounds immediately following the procedure to prevent excessive blood loss by the patient.

Figure 1:
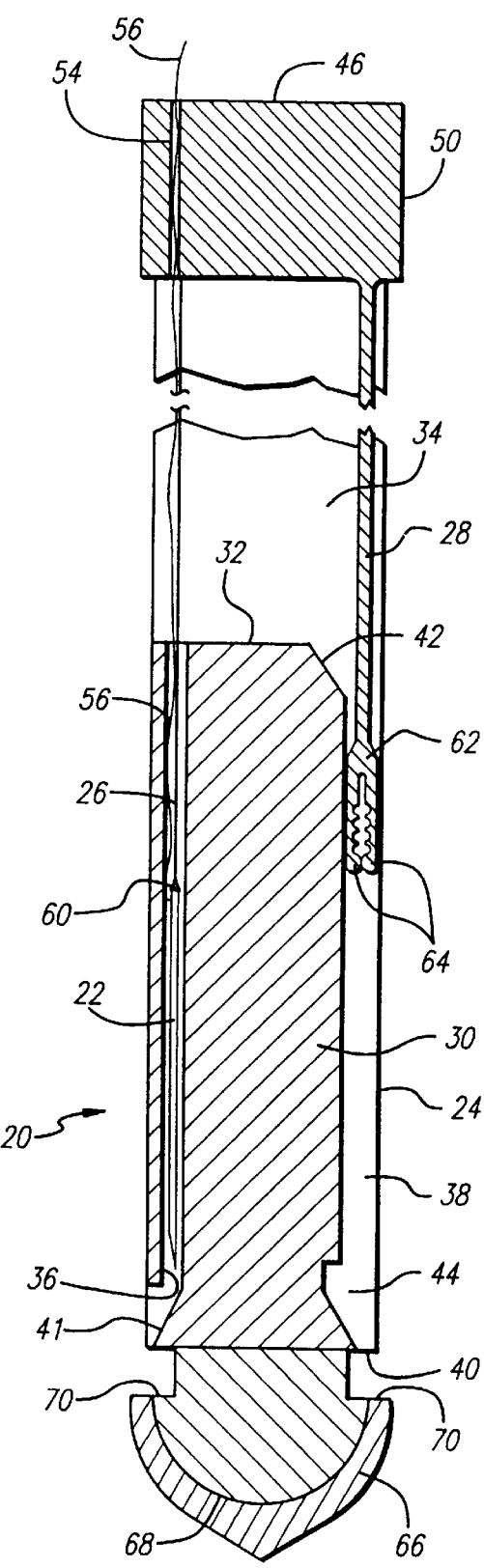
FIG. 1 depicts a cross-sectional front elevational view of a suturing apparatus embodying the present invention.

Suturing assembly 20 in FIG. 1 consists primarily of elastically precurved needles 22 maintained in a linear configuration within a guide body 24 containing needle ejectors 26 for ejecting the needles out of the guide body and needle receivers 28 for receiving and retracting the needles back into the guide body.

In keeping with the preferred embodiment, referring to FIG. 1, guide body 24 has an elongated, cylindrical configuration with a solid core 30 defining a handle stop 32 with its proximal end. The guide body is formed with a handle chamber 34 at the proximal end. Laterally opposed bores 36 and 38 extend parallel to the axis of the body from distal end 40 to handle chamber 34. Ejection bore 36 is formed with ejection ramp 41 extending to distal end 40 at an angle with respect to the ejection bore. Retraction bore 38 is formed at its proximal end with compression ramp 42 extending at an angle from the retraction bore to the handle stop and at its distal end with expansion chamber 44 communicating with guide body distal end 40.

Referring to FIGS. 1 and 3, handle 46 is slidably disposed within handle chamber 34 and is connected through handle beams 48 to outer handle band 50. Handle beams 48 are slidably removably maintained in longitudinal slots 52 formed in the side of body 24 along the length of expansion chamber 34. Handle 46 also includes vertical suture aperture 54. Referring to FIG. 1, ejector arm 26 extends from the distal end of handle 46 adjacent to suture aperture 54 and is linearly configured to be slidably received within ejection bore 36 with sufficient tolerance to fit within the ejection bore concurrently with suture 56.

Needle 58 is positioned in ejection bore 36 underneath ejector arm 26 with the pointed end downwardly disposed, and is formed with bore 60 in its upwards facing proximal end to receive suture 56 therethrough. Receiver arm 28 extends from the distal end of handle 46 laterally opposed to ejector arm 26 and is slidably received in retraction bore 38. Receiving forceps 62 are attached to the distal end of receiver arm 28 and are equipped with jaws 64 configured to receive and secure needle 58 therebetween.

Figure 2:
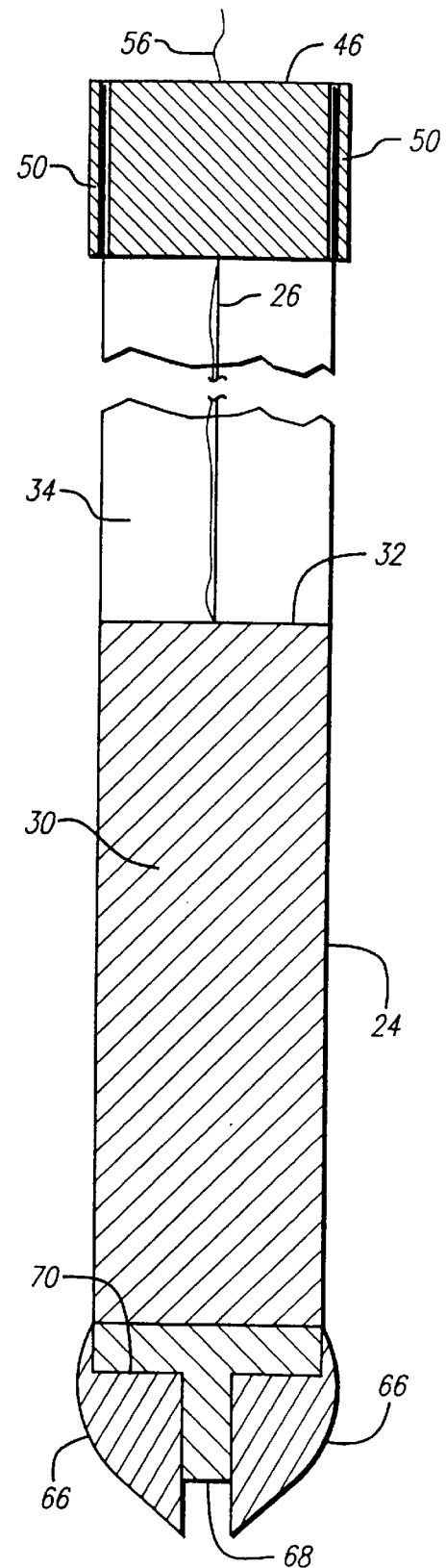
FIG. 2 depicts a cross-sectional side elevational view of the suturing apparatus shown in FIG. 1.

Referring to FIGS. 1 and 2, guide tip 66 is attached to guide body distal end 40 and is formed with a generally spherical configuration. Guide channel 68 extends across the surface of tip 66 from beneath ejection bore 36 to beneath retraction bore 38. Guide tip 66 is further configured with notches 70 extending across its proximal end beneath the guide body bores, and of sufficient width to define grooves between the tip and guide body distal end 40 for receipt of lumen tissue therein. Needle 58 must be of sufficient length to extend from the distal end of ejection bore 36 across guide channel 68 and into expansion chamber 44, and forceps 62 must be at sufficient elevation with respect to ejector arm 26 such that jaws 64 are fully expanded within expansion chamber 44 when ejector arm 26 is disposed adjacent to distal end 40 of guide body 24.

Guide body 24 and handle 46 can be formed from any material affording the desired characteristics of durability, non-toxicity, and low frictional resistance. Because the overall configuration of both pieces is somewhat complex, it is cost advantageous to use easily cast or extruded materials, such as plastics, ceramics, glass, and metals. Receiving forceps 62 must be formed from a resilient material that can withstand closing and opening of the jaws 64, and should preferably also offer reduced frictional resistance when sliding within retraction bore 38. Guide tip 66 should be manufactured from a material that will not contaminate the patient's blood stream, and that is compatible with conventional bonding methods for easy and permanent attachment to guide body 24.

Figure 7:
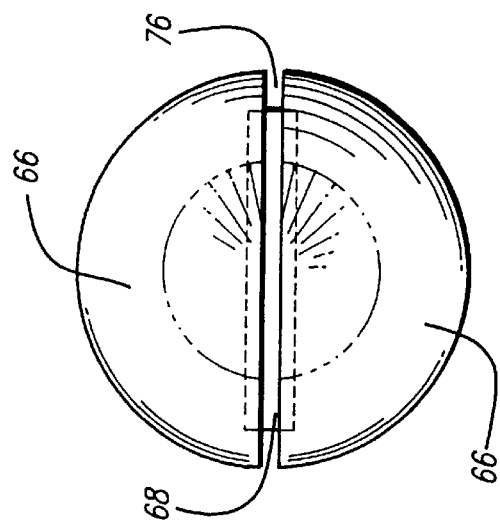
FIG. 7 depicts a bottom view of the tip of the suturing apparatus shown in FIG. 1.

Referring now to FIG. 7, needle 58 must be formed from a material that will resiliently maintain a linear configuration when positioned within either bore of guide body 24 and when released from the bore will begin to elastically assume a curved configuration at a predetermined rate to substantially conform to the surface of guide channel 68. The needle may therefore be manufactured from spring steel or from alloys exhibiting shape memory properties. Articles manufactured from such alloys may be deformed from their original shape into a different configuration that is heat unstable, and upon the application of heat will revert to the original configuration. Certain shape memory alloys, including superelastic nickel-titanium (NiTi) or copper-zinc-aluminum (CuZnAl) alloys that are well known in the art, can be deformed through the application of stress to the article of manufacture and will revert to their original shape upon removal of the stress in a phenomenon generally referred to as stress induced martensite (SIM), thereby eliminating the need for alternately cooling and heating the article. SIM shape memory alloys that are stressed at temperatures between where the alloy first begins to transform from austenite to martensite, and the maximum temperature at which martensite can occur, deform elastically up to a critical stress and then continue to deform through the formation of SIM. When the deforming stress is removed and the alloy is at a temperature above that at which it starts to revert back to austenite, the alloy will attempt to return to its original shape. The temperature at which the alloy begins to revert to the stable austenite phase varies with the composition of the alloy, and it is obviously preferable for the practice of the present invention that the SIM shape memory alloy selected for making needle 50 is one that reverts back to austenite at the typical human body temperature of no more than about 98° F. Needle 50 also requires a sharp tip to penetrate tissue, and materials may be bonded to the shape memory alloy that will provide an improved sharp edge.

In conjunction with the suturing apparatus of the present invention, the preferred method of use is herein described. The apparatus is prepared for use by first threading suture 56 through needle bore 60 and attaching it thereto, then inserting needle 58 into ejection bore 36 with the sharp end disposed downwardly towards guide body distal end 40. Suture 56 is next threaded through suture aperture 54 in handle 46. Referring now to FIGS. 1 and 3, handle 46 is next inserted into handle chamber 34 such that handle beams 48 engage longitudinal slots 52 formed in the wall of the guide body 24, and ejector arm 26 and receiving forceps 62 are received in ejection bore 36 and retraction bore 38, respectively.

Referring now to FIGS. 6A–6C, once the suturing apparatus has been prepared for use, it is inserted into a puncture wound formed in a body lumen beneath tissue 72 such that lumen walls 74 are engaged by the grooves formed between guide body 24 and tip 66. The operator of the apparatus can now grasp guide body 24 with one hand and handle band 50 with the other hand and commence to move handle 46 towards distal end 40, thus urging ejector arm 26 to drive needle 58 out of ejector bore 36 and pierce lumen wall tissue 74. Ejection ramp 41 guides needle 58 towards guide channel 68 as needle 58 begins to exit ejection bore 36. Lumen tissue 74 is supported by the tip notch 70 underlying the ejection bore, and thus the ease with which needle 58 pierces tissue 74 is significantly enhanced.

Referring to FIG. 7, as needle 58 is ejected out of ejection bore 36, it begins to curve back around the surface of guide channel 68 at a predetermined rate, and eventually reaches tip notch 70 underlying retraction bore 38 where it pierces the lumen tissue 74 directly opposite the wound from the first incision of needle 58. The tissue is also supported by the groove between body 24 and tip 66 formed underneath the retraction bore, thereby enhancing the ease of puncture by needle 58. The needle's natural tendency to curve back along the guide channel is a function of the material selected and may thus exhibit in different manners under different conditions. SIM shape memory alloys, for instance, will immediately attempt to curve back once released from the stress imposed by ejection bore 36, as long as the alloys revert to the stable austenite phase at a temperature of no more than about 98° F. Spring steel, on the other hand, is typically not dependent upon temperature to begin transforming back to its curved configuration.

Referring to FIGS. 5A–5C, as ejector arm 26 is being displaced downwards, receiver arm 28 is also being displaced in the same direction and by an equal amount, such that both receiving forceps 62 and needle 58 reach expansion chamber 44 concurrently. As forceps 62 begin to enter the expansion chamber, jaws 64 begin to expand apart and receive advancing needle 58 therebetween. Handle 46 eventually runs against handle stop 32, at which time ejector arm 26 is flush with distal end 40 of guide body 24, and needle 58 is completely ejected out of ejection bore 36. At this time the operator will begin to move handle 46 upwards, thereby urging forceps 62 back into retraction bore 38 and causing jaws 64 to come together and grasp the tip of needle 58 therebetween. The jaws are preferably made from a high friction material such as rubber or similar material to enhance the grasping ability upon the smooth surface of needle 58. In addition, the needle may be formed with a barb or other protuberance near the tip that will also aid the jaws in grasping and retaining the needle as the forceps are retracted back into the guide body. The needle is thus retracted along with the forceps into retraction bore 38, and as it is pulled through lumen tissue 74 it pulls suture 56 along with it. As the needle enters retraction bore 38 it begins to assume the linear configuration of the bore, either by deforming elastically as in the case of spring steel or by transforming into martensite in the case of SIM memory shape alloys, and thus allows the operator to fully retract needle 58 out of the lumen tissue and leave behind a length of suture to tie together and thereby seal the wound closed.

It will be appreciated by those skilled in the art that the operator of the apparatus may choose to apply any practical number of additional sutures at various angles to the other sutures, and thereby seal larger, profusely bleeding wounds. The apparatus of the present invention is not restricted to puncture wounds, but also may be employed to seal linear incisions by applying suture across the incision at predetermined intervals along its length.

Figure 9:
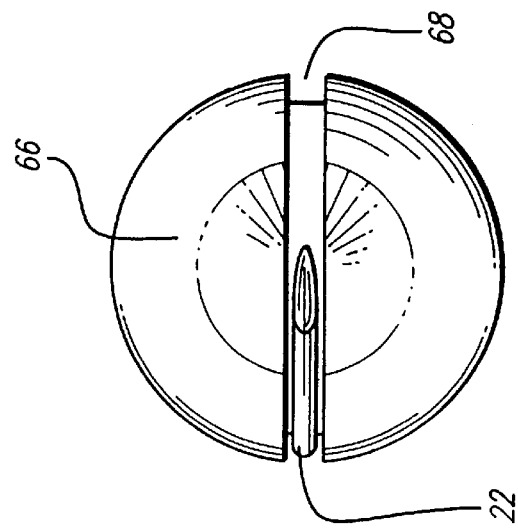
FIG. 9 depicts a bottom view of the tip of the suturing apparatus shown in FIG. 3.

In addition, many variations and modifications to the preferred embodiments described above may be practiced to adapt the apparatus of the present invention to various applications. For example, as shown in FIGS. 4 and 9, tip 66 may be formed with an enclosed guide channel 68 and a suture escape slot 76 to allow removal of suture 56 when the apparatus is removed from within the patient's body. This configuration would minimize the potential for inadvertently engaging body tissue with the tip 66 as it is being inserted into the wound, and would also eliminate any risk of needle 58 accidentally curving in the wrong direction, such as perhaps due to incorrect insertion into ejection bore 36.

Figure 8:
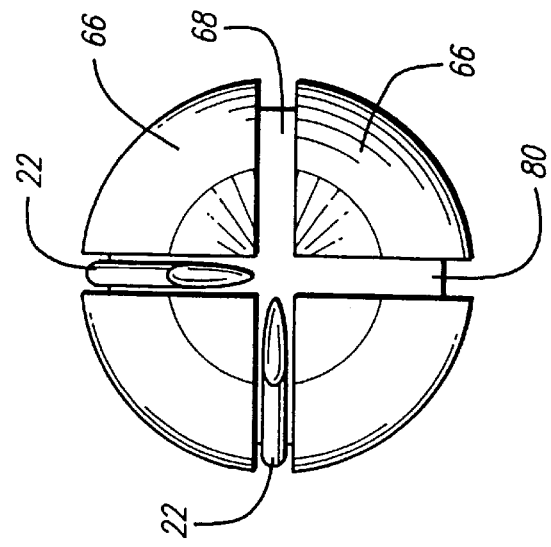
FIG. 8 depicts a bottom view of the tip of a multi-needle suturing apparatus embodying the present invention.

Suturing apparatus 20 also may be formed with more than one pair of ejection and retraction bores. As shown in FIG. 8, for example, the apparatus may have two pairs of corresponding bores with two needles 58 and 78 piercing the lumen tissue simultaneously, thus allowing medical staff to seal a wound shut in a minimum of time. Such an embodiment has two guide channels 68 and 80 running across the surface of tip 66, preferably at right angles to each other, and guide channel 80 is recessed from guide channel 68 within tip 66 to avoid interference between the two needles as they advance across the tip. Larger diameter apparatuses may be formed with three or more pairs of bores, thus allowing instantly suturing relatively large wounds and greatly minimizing the risk of inadvertent post operative damage to the patient. Apparatus embodying the present invention may also be manufactured with guide bodies having planar configurations and multiple pairs of corresponding bores aligned longitudinally along an elongated tip, so that the operator of the apparatus may simultaneously suture closed a portion of a linear incision.

It must be appreciated that the present invention also may be embodied in an apparatus that utilizes mechanical, electrical, hydraulic, or pneumatic means to advance and retract the needles, such as by employing an electric motor to insert and retract handle 46, or by alternately filling and draining the ejection and retraction bores with fluid or gas. In addition, a compression spring may be positioned within handle chamber 34 to automatically urge handle 46 away from handle stop 32 and back into the fully retracted position.

From the foregoing, it will be appreciated that the present invention provides a method and an apparatus for suturing small, as well as large, wounds in body tissue with a high degree of accuracy and repeatability, and in a minimum of time. The present invention overcomes many problems associated with the prior art by providing an extremely simple apparatus that may be cheaply and easily manufactured in very small diameters, and may thus be custom made to fit wounds of any size. The method of the present invention produces a clean, tight seal in which the suture encircles the wound without passing through it, and thereby allows quicker closure and healing of the severed tissue. The apparatus taught by the present invention does not utilize members that expand inside the patient's body, and thus eliminates the risk of incidental damage caused to the patient by an inattentive or inexperienced operator. The device is also simple and cheap enough to manufacture as a single use, throw away device that will not adversely impact the costs of intraluminal procedures, rather it will reduce them in terms of much shortened recovery times and minimized risk of post operative trauma.

While particular embodiments of the invention have been illustrated and described, various modifications can be made without departing from the spirit and scope of the invention, and all such modifications and equivalents are intended to be covered.

What is claimed is:

1. A method for suturing a wound in a body lumen, comprising the steps of:

providing a suturing assembly having an elongated guide body with a central axis and a distal end and formed with at least one pair of axially parallel, laterally opposed first bores and second bores extending from the distal end through at least a portion of the body, a tip attached to the distal end of the body and formed at least in part with a semi-spherical configuration and having a tip surface, and a pair of resilient, elastically precurved needles removably positioned in each respective first bores and each having a proximal end with suture material secured thereto;

positioning the tip within the wound with the lumen tissue located directly underneath the bores;

advancing the needles out of the respective first bores, piercing the lumen tissue, curving around the tip surface, and repiercing the lumen tissue and entering the respective second bores;

grasping the needles as each advances into the respective second bores;

retracting the needles into the second bores;

pulling the sutures through the lumen tissue; and tying the sutures to seal the wound.

2. The method as set forth in claim 1, wherein the needles are advanced out of the respective first bores by an ejector arm slidably positioned proximal to the proximal end of each needle.

3. The method as set forth in claim 2, wherein the needles are pulled into the respective second bores by a pair of needle receivers slidably positioned one each in the second bores, each needle having two or more resiliently expandable jaws to grip the needles.

4. The method as set forth in claim 3, wherein the ejector arms and needle receivers are axially displaced by a handle.

5. The method as set forth in claim 3, wherein the ejector arms and needle receivers are displaced by at least one electric motor.

6. The method as set forth in claim 3, wherein the ejector arms and needle receivers are displaced pneumatically.

7. The method as set forth in claim 3, wherein the ejector arms and needle receivers are displaced hydraulically.

8. The method as set forth in claim 1, comprising the further steps of:

provide the tip with notches facing each bore to form a groove between the tip and the distal end of the guide body; and positioning the tip in the wound to receive and support the lumen tissue in the grooves.

9. The method as set forth in claim 1, comprising the further step of:

providing the tip with channels across a surface thereof to guide each needle from the respective first bore to the corresponding second bore.

10. The method as set forth in claim 1, comprising the further step of:

providing the tip with a pair of needle channels to guide each needle from the respective first bore to the corresponding second bore, and further providing suture escape slots on a surface of the tip.

11. The method as set forth in claim 1, comprising the further step of:

applying heat to the needles to induce a thermal phase change in the material causing the needles to curve around the tip.

12. The method as set forth in claim 1, comprising the further step of:

cooling the needles to induce a thermal phase change in the material causing the needles to curve around the tip.

13. The method as set forth in claim 1, comprising the further step of:

applying an electric current to the needles to induce a thermal phase change in the material causing the needles to curve around the tip.

* * * * *